United States Patent [19]

Theeuwes

[11] 4,410,328
[45] Oct. 18, 1983

[54] DISPENSING DEVICE WITH INTERNAL DRIVE

[75] Inventor: Felix Theeuwes, Los Altos, Calif.

[73] Assignee: Alza Corporation, Palo Alto, Calif.

[21] Appl. No.: 281,952

[22] Filed: Jul. 10, 1981

[51] Int. Cl.³ .............................................. A61M 7/00
[52] U.S. Cl. .................................... 604/892; 604/890
[58] Field of Search ............ 128/260, 213 R, 261–272; 604/890, 891, 892, 895; 424/19–24

[56] References Cited

U.S. PATENT DOCUMENTS 3,995,632 12/1976 Nakano et al. ...................... 128/260

Primary Examiner—Richard J. Apley
Assistant Examiner—T. J. Wallen
Attorney, Agent, or Firm—Paul L. Sabatine; Edward L. Mandell; Steven F. Stone

[57] ABSTRACT

A device is disclosed for delivering a beneficial agent. The device comprises (1) a housing defining an internal space (2) a piston in the housing separating the space into an agent compartment and a power compartment, or a flexible container in the space, (3) an opening in the housing connecting the agent compartment or the container with the exterior of the housng, and (4) an osmotic device in the power compartment or beneath the container.

1 Claim, 3 Drawing Figures

DISPENSING DEVICE WITH INTERNAL DRIVE

AREA OF THE INVENTION

The invention pertains to a novel and useful self-contained dispensing device with an internal drive. The device delivers an useful agent to an environment of use.

BACKGROUND OF THE INVENTION

Over the past decade, much research has been devoted to developing new and useful devices for delivering beneficial agents to agent receptor environments of use. For example, in U.S. Pat. No. 3,760,984 issued to Theeuwes, there is disclosed a device comprising an inner collapsible container carrying on its outer surface a layer of an osmotic solute and a distant layer of a polymer permeable to fluid and impermeable to solute. The device has a means for filling the container. In U.S. Pat. No. 3,971,376, issued to Wichterle, a device is disclosed comprising a capsule having a unitary wall formed of a substantially noncollapsible elastic material that maintains a constant volume and is exposed to the environment of use. A textile fabric is imbedded in the elastic material to strengthen the material and act as a reinforcement. In U.S. Pat. No. 3,987,760 issued to Eckenhoff et al., there is disclosed a fluid flow moderator comprising a conduit that fits into an osmotic device to provide an outlet for dispensing fluid from the device. In U.S. Pat. No. 3,995,631 issued to Higuchi et al., there is disclosed a bag formed of a flexible material encapsulated with an osmotically effective solute surrounded by a wall having in at least a part controlled permeability to an external fluid. The above-described devices are useful for delivering many agents, and they represent a valuable contribution to the delivery art. The present invention is a further advancement in the delivery art by making available a novel device having a new internal power profile for activating and driving the device.

BRIEF DESCRIPTION OF THE DRAWINGS

In the drawings, which are not drawn to scale, but are set forth to illustrate various embodiments of the invention, the figures are as follows.

In the drawings and specification, like parts in related Figures are identified by like numbers. The terms appearing earlier in the specification and in the description of the drawings, as well as embodiments thereof are described later in the specification.

DETAILED DESCRIPTION OF THE INVENTION

Figure 1:
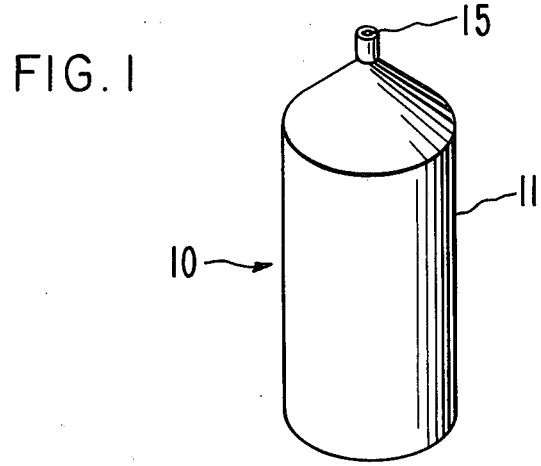
FIG. 1 is a view illustrating the dispensing device provided by the invention.

Turning now to the drawings in detail, which are examples of new and useful devices for dispensing an agent, and which example is not to be construed as limiting, one example is illustrated in FIG. 1 by the numeral 10. In FIG. 1, device 10 comprises a housing 11 sized, shaped and adapted for placing device 10 in an environment of use.

Figure 2:
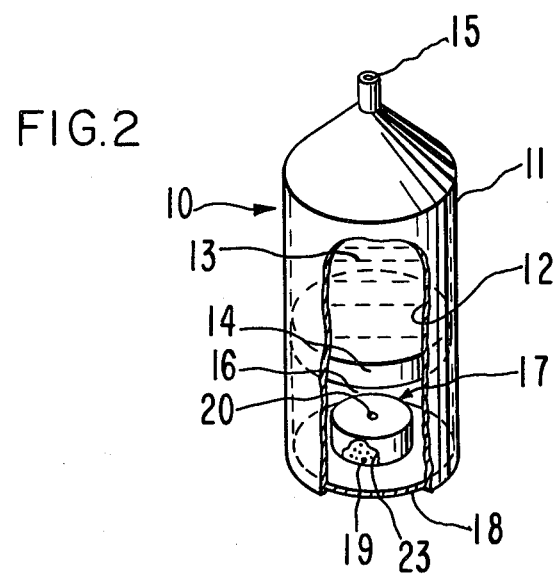
FIG. 2 is an opened view of the device of FIG. 1 illustration one internal structure of the device.

In FIG. 2, housing 11 is made of wall 12, which is seen in opened-section. Wall 12 surrounds and defines agent compartment 13 and driving compartment 16. A piston 14 separates compartment 13 and compartment 16. Wall 12 is made from a rigid wall forming material, such as, polyethylene, polypropylene, nylon and the like. Housing 11 has an opening 15 through which agent compartment 13 communicates with the exterior of device 10. When device 10 is in operation, agent in compartment 13 is dispensed from device 10 through opening 15. Piston 14 fits snugly against the internal wall of device 10. Piston 14 is made of rubber, nylon, polytetrafluoroethylene and the like. Compartment 16 contains an osmotic device 17 setting on a retaining member 18. Retaining member 18 can be manufactured as part of wall continuous with housing 11, it can be manufactured separately and then inserted or joined to housing 11 after the components have been placed inside housing 11, it can extend around the outer periphery on the bottom of the housing, it can be a screen, or member 18 can comprise a plurality of holes in housing 11. Retaining member 18 can be made from the same materials forming housing 11, or it can be made from other suitable materials. In its design and manufacture, member 18 permits an external fluid to enter device 10 and become available to osmotic device 17. Device 10 can optionally be made as a reusable device. That is, agent compartment 13 can be refilled, and osmotic device 17 in compartment 16 can be replaced with the refilling of agent compartment 13.

Osmotic device 17, used for powering device 10 is disclosed in U.S. Pat. No. 3,845,770 by Theeuwes et al. Device 17 comprises a semipermeable wall 23 that surrounds an osmotic agent compartment containing said agent and represented by dots 19. A passageway 20 through semipermeable wall 23 connects compartment 19 with the exterior of osmotic device 17, the space between it and the bottom of piston 14. The osmotic agent exhibits an osmotic pressure gradient across semipermeable 23 against an external fluid that enters device 17. Various osmotically effective solutes include sodium chloride, lithium chloride, potassium chloride, sodium sulfate, and the like. Semipermeable wall 23 is formed of cellulose acylate, cellulose diacylate, cellulose triacylate, cellulose acetate, cellulose diacetate, cellulose triacetate, and the like. In operation, fluid is imbibed through semipermeable wall 23 into osmotic device 17 to form a solution of the osmotic solute that is pumped from the osmotic device 17. The fluid fills the space between osmotic device 17 and the bottom of piston 14, moving piston 14 forward in housing 11. As piston 14 moves toward opening 15 it urges agent from agent compartment 13 to the exterior of device 10. Agents that can be dispensed by device 10 include drugs, antibacterials, antifungals, plant growth promoters, surfactants, chemical reactants, and the like.

Figure 3:
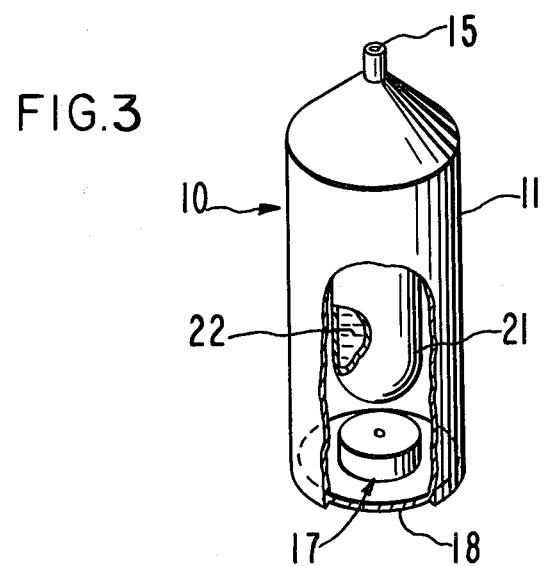
FIG. 3 is an opened view of the device of FIG. 1 illustrating another internal structure of the device.

FIG. 3 illustrates another dispensing device 10 provided by the invention. In FIG. 3, housing 11 of device 10 is seen with a section of wall 12 removed for illustrating the internal structure of device 10. In FIG. 3, device 10 has an internal disposed container 21 made of a flexible materials. Representative materials are elastomeric materials such as natural rubber, often identified by the synonyms poly(2-methyl-1,3-butadiene) and cis-1,4-polyisoprene, butadiene-styrene copolymer and the like. Container 21 at its top can be sealed to the inside of housing 11, or container 21 can have a neck that connects to opening 15. A beneficial agent 22 is housed in container 21. Beneficial agent 22 is released from container 21 through opening 15. Immediately below container 21 is osmotic device 17 resting on retaining member 18. Structures 17 and 18 were described above. In operation, agent 22 is dispensed from device 10 by osmotic device 17 imbibing fluid into device 17 to form a solution that is pumped from device 17. The fluid contacts and applies pressure against container 21 causing container 21 to collapse. As container 21 collapses, agent 22 therein is urged from the container 21 through opening 15 to the exterior of device 10.

Although the foregoing invention has been described in detail by way of full disclosure, it will be understood that changes and modifications may be practiced within the scope of this invention.

I claim:

1. A dispensing device for delivering a beneficial agent to an environment of use, the dispensing device comprising:
   (a) a housing comprising a shape retaining wall that defines an internal space, which housing has at its top an opening that connects the space with the exterior of the housing, and at its bottom a retaining member that lets an external fluid enter the housing;
   (b) a piston in the housing that fits against the internal wall of the housing;
   (c) a beneficial agent compartment for storing a beneficial agent in the housing, the beneficial agent compartment defined by the space below the top opening and above the piston; and,
   (d) a driving compartment in the housing, the driving compartment defined by the space above the retaining member and below the piston, the driving compartment containing an osmotic device comprising:
      (1) a semipermeable wall that surrounds;
      (2) an osmotic agent compartment containing an osmotically effective solute, with;
      (3) a passageway through the semipermeable wall connecting the osmotic agent compartment with the exterior of the osmotic device, and wherein when in operation, beneficial agent is delivered from the dispensing device by (4) external fluid entering the dispensing device through the retaining member, and (5) being imbibed through the semipermeable wall into the osmotic agent compartment of the osmotic device to, (6) form a solution containing the osmotic solute that is pumped through the passageway from the osmotic device that, (7) fills the driving compartment, thereby (8) urging the piston forward in the dispensing device, and (9) concomitantly dispensing beneficial agent through the top opening to the environment of use.

* * * * *